United States Patent [19]

Bell et al.

[11] Patent Number: 5,584,790
[45] Date of Patent: Dec. 17, 1996

[54] VARIABLE INCLINATION CENTRIFUGATION ASSEMBLY FOR RAPID SEPARATION OF BLOOD

[75] Inventors: Michael L. Bell, Fullerton; Winston H. Lowe, Sunnyvale, both of Calif.

[73] Assignee: Beckman Instruments, Inc., Fullerton, Calif.

[21] Appl. No.: 525,112

[22] Filed: Sep. 8, 1995

[51] Int. Cl.⁶ .................................................... B04B 5/02
[52] U.S. Cl. ............................................. 494/20; 494/37
[58] Field of Search ................................ 494/1, 7, 16, 20, 494/21, 31, 33, 37, 84, 85; 210/782

[56] References Cited

U.S. PATENT DOCUMENTS

| | | |
|---|---|---|
| 3,393,864 | 7/1968 | Galasso et al. ............................ 494/20 |
| 3,786,986 | 1/1974 | Guerrero .................................. 494/20 |
| 3,935,995 | 2/1976 | Williams et al. ......................... 494/20 |
| 4,221,324 | 9/1980 | Frey . | 
| 4,769,000 | 9/1988 | Van Heel ................................ 494/20 |
| 4,846,974 | 7/1989 | Kelley et al. . | 
| 4,981,585 | 1/1991 | Kelley et al. . | 
| 5,030,341 | 7/1991 | McEwen et al. . | 
| 5,308,506 | 5/1994 | McEwen et al. . |

Primary Examiner—Charles E. Cooley
Attorney, Agent, or Firm—William H. May; Janis C. Henry

[57] ABSTRACT

A variable inclination centrifugation or rotor assembly and a method for rapid separations. The samples, such as whole blood, are centrifuged within pivoting tube holders while in a first position wherein the longitudinal axes of the tube holders are substantially parallel to a central axis of rotation. As rotation continues, the tube holders are inclined in a radial direction by controlled adjustment of the tube holders toward a second position wherein the axes of the tube holders and the rotation axis are substantially perpendicular. The first embodiment of the assembly employs a worm gear to incline the samples and allows for inclination and rotation of the samples to be controlled independently. The second and third embodiments employ a spring-loaded linkage system and a governor mass and three-arm linkage system, respectively, for inclination. These are activated by the rotational speed of the samples. The assemblies of the present invention may be utilized within standard centrifuges, and may be removed from the centrifuge, as for sterilization.

27 Claims, 5 Drawing Sheets

VARIABLE INCLINATION CENTRIFUGATION ASSEMBLY FOR RAPID SEPARATION OF BLOOD

TECHNICAL FIELD

This invention relates to instruments and methods for separating whole blood into its components.

BACKGROUND ART

Most clinical chemistry analysis requires a separated blood sample. Separation of a usable sample from whole blood is traditionally achieved by centrifuging blood collection tubes for several minutes. The current practice is for tubes be spun for approximately 10 to 15 minutes at 1200 g.

The current method has several drawbacks, however. First, the blood separation time delays delivery of analytical results. Second, the long separation time requires large centrifuge batch sizes in order to maintain high sample throughput during blood processing. This necessitates the use of large, expensive centrifuges.

Rapid blood separation systems have been developed. For example, see U.S. Pat. Nos. 5,030,341 and 5,308,506 to McEwen et al. These patents describe specialized blood separation tubes and a specialized instrument for rotating the tubes about a longitudinal axis. U.S. Pat. Nos. 4,846,974 and 4,981,585 to Kelley et al. disclose disk-shaped cassettes for centrifugal separation of blood with a high speed rotary drive. All of the above systems require specialized blood collection or separation containers in addition to dedicated instruments, which add a continuing burden to the overall cost of the system.

What is needed is a blood separation system and method which is easy to use, contributes to the low cost operations of the laboratory, and rapidly provides a separated blood sample.

DISCLOSURE OF THE INVENTION

The above objects have been achieved with a variable inclination centrifugation assembly and method for rapid separation of samples, such as blood, which have components of differing densities. In a first phase, the samples, which are contained within tubes and tube holders, are rotated about a central axis of a yoke which supports the tube holders, while the tube holders are in a first position in which the longitudinal axes of the tube holders are substantially parallel to the axis of rotation. In a second phase, the tube holders are carefully and gradually inclined outwardly or radially, while rotation continues, toward a second position in which the longitudinal axes of the tube holders are substantially perpendicular to the rotation axis.

The method of the present invention allows for rapid separation because spinning of the sample initially, i.e. in the first phase, allows the sample to travel a distance equal to less than the diameter of the tube. This causes preliminary separation of the sample components. As the tube holders are inclined, the separation of sample components is refined and stabilized as the sedimented sample components travel toward the bottom of the tube. The decrease in separation time may be twelve-fold over conventional methods.

The first embodiment of the variable inclination centrifugation assembly includes a rotation subassembly and an inclination subassembly preferably utilizing a worm gear. A separate rotation motor and inclination motor are utilized, and the rotation and inclination aspects of the separation may be independently controlled. Because the worm gear is engaged, the tube holders do not swing freely, but rather become inclined upon operation of the inclination subassembly.

The second embodiment of the centrifugation assembly utilizes a spring-loaded linkage system in which the spring-loaded linkages are activated by the rotational speed of the samples and cause the inclination. Each tube holder is coupled via one spring-loaded linkage to an anchor ring that is positioned about the central hub of the centrifugation assembly. Housed within each linkage are a compression spring and an extension rod. At rest and during low speed rotation, the tube holders are each held in the first position by the associated spring-loaded linkage, whose overall length is dependent upon the force exerted by its internal compression spring. As the speed of rotation increases, the forces arising from centrifugation overcome the spring force within the linkage and allow the extension rod to compress the spring and thus extend the length of the spring-loaded linkage. This action of the spring-loaded linkages causes the tube holders, which are connected to the yoke at pivot points, to become inclined toward the second position. Through the use of appropriately-sized compression springs, the inclination occurs gradually, so as not to disrupt the sample.

The third embodiment includes a governor-based linkage system. An adjustable governor mass in combination with a set of three arms extending from the mass is associated with each of the tube holders in this embodiment. One of the three arms of each governor-based linkage is connected to one of the tube holders, another arm is connected to the yoke or hub of the centrifugation assembly, and a third arm is connected to a universal collar that slides about the hub of the centrifugation assembly. A resistance spring is also positioned about the hub and presses down upon the sliding collar, thereby retaining the tube holders in the first position at rest and at low speeds. As rotational velocity increases, however, each governor mass is driven outward from the hub. This outward drive compresses the resistance spring to establish an equilibrium position for each speed. Each governor mass with its associated three arms moves in an outward direction from the hub, thereby causing pivoting of the tube holders and inclination of the samples within the tube holders. As with the second embodiment, an appropriately-sized spring may be used to ensure gradual and synchronized inclination of the samples and to maintain balance within the assembly.

An advantage of the present invention is that separation of the samples occurs rapidly and, in the case of blood samples, conventional blood draw tubes may be used. Additionally, the assemblies need not be fixed parts of the centrifuge. Therefore, they may be utilized in conjunction with standard centrifuges and may be removed from the centrifuge for sterilization temperature control, or remote sample preparation.

BEST MODE FOR CARRYING OUT THE INVENTION

Figure 1:
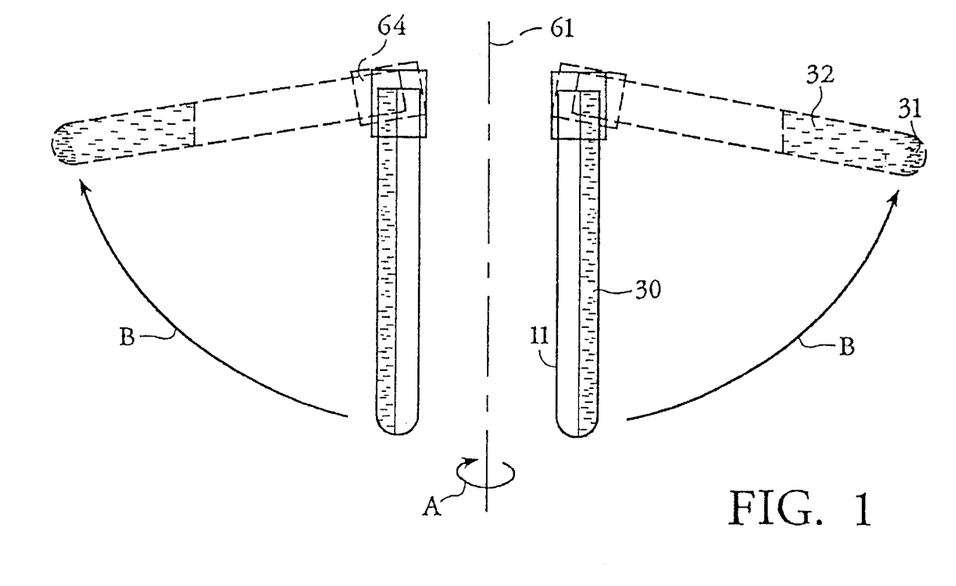
FIG. 1 illustrates the effects of the motions and relative positions of the tubes upon the samples.

With reference to FIG. 1, the relative positions of a sample within a tube, according to the method of the present invention, is shown. Balanced tubes are initially held in a first position in which the longitudinal axes of the tubes are substantially parallel to the rotation axis 61. The tubes are rotated about axis 61, as shown in FIG. 1 by arrow "A." Rotation while the tubes are in this first position causes the denser elements of the sample, such as red blood cells in whole blood, to settle along the outer walls of the tubes. The time required for the settling is short compared to conventional centrifugation, as the cells need to travel only about half the tube diameter. Cells in tubes spun conventionally, by contrast, must settle about half the length of the tube.

Preferably after the majority of cells have settled, the tubes are inclined with respect to the rotation axis 61. The result is that the angle between the longitudinal axis of each tube and the rotation axis 61 increases from near zero to near ninety degrees, as shown by arrows "B" in FIG. 1. Thus, the longitudinal axes of the tubes and the rotation axis 61 begin in a substantially parallel position and are shifted to a substantially perpendicular position with respect to each other. Rotation continues during this inclination change. The purpose of the inclination change is to shift the separated layers of blood or other sample from an arrangement which is stable only under rotation to one which is stable without rotation. To accomplish this, the inclination change should be gradual. An abrupt tilt may remix the pellet with the supernatant.

After the inclination change is complete, the tube rotation may stop. For a blood sample, this leaves the cells at the bottom of the tube and supernatant, e.g. serum or plasma, above. It is desirable to restore the tube to the first position for ease of handling. This can be done after the rotation has stopped or as the rotation is stopping. If the latter method is chosen, then it is important that the rotation be sufficiently slow during this restoration so that the sample components do not reorient to the arrangement achieved during the earlier phase. An appropriate rotation speed during this restoration is one where the resultant centrifugal force is less than the gravitational force. The nature of the sample dictates the degree of inclination and the top speed of rotation necessary for the separation process.

In FIG. 1, tubes 11 containing samples of whole blood 30 are shown. During the first phase, the samples generally travel toward the outer walls of the tubes. The second phase allows for further separation into a serum or plasma supernatant 32 and a pellet of blood cells 31.

For the initial phase, the tubes need not be oriented exactly parallel to the rotation axis. A slight positive inclination, with the bottoms of the tubes further from the rotation axis than the tops of the tubes, reduces or eliminates hydrodynamic forces on the tube stoppers 64. This may be desirable to prevent ejection of the stopper and loss of the sample. Also, the assembly need not be oriented so that the rotation axis is vertical.

Figure 2:
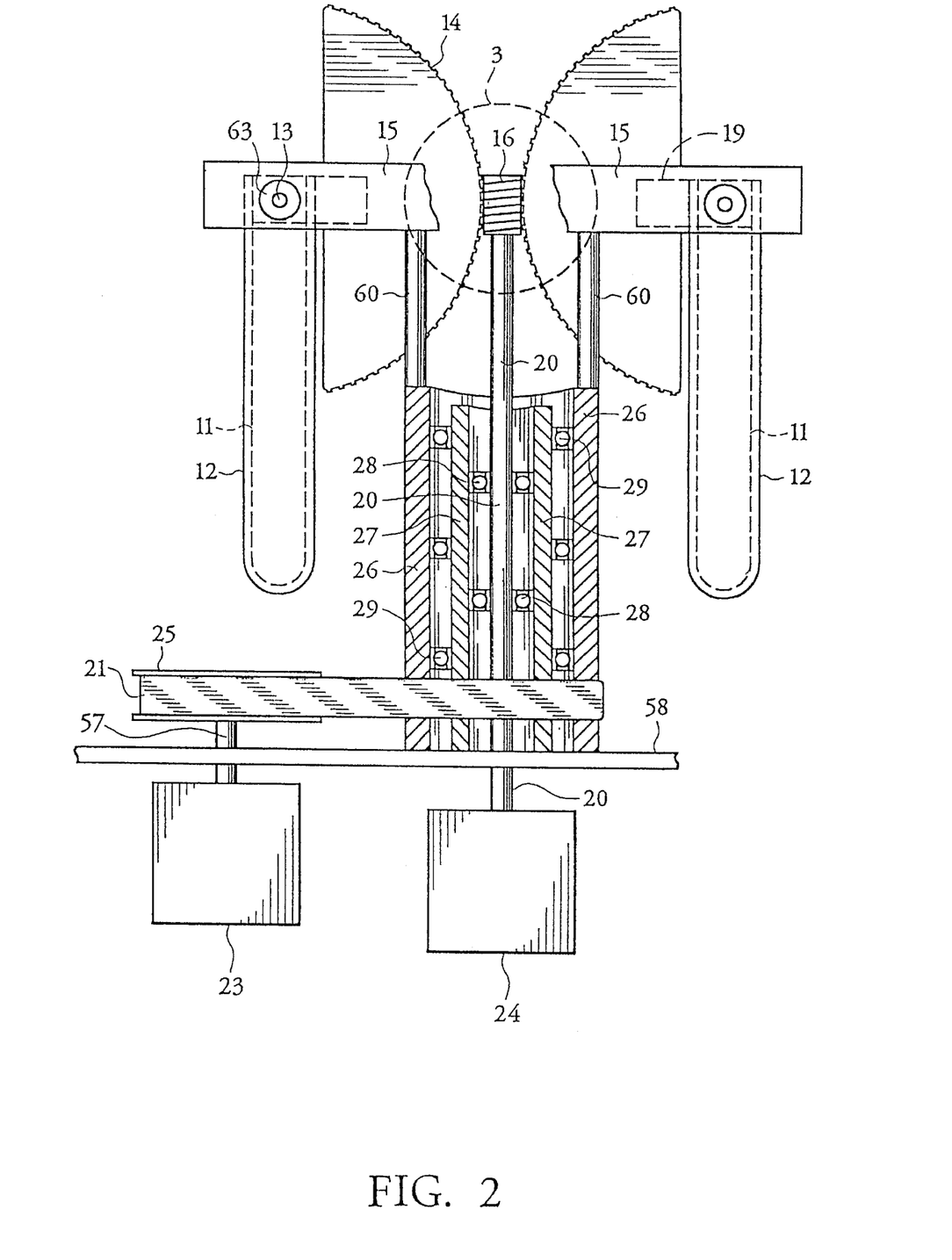
FIG. 2 is a side view of the centrifugation assembly according to the first embodiment of the present invention, with a sectional view of the hub.

FIG. 2 shows a centrifugation assembly of the present invention, according to a first embodiment. This first embodiment allows for independent control of the rotation and inclination in the centrifugation process, and is the preferred embodiment. In FIG. 2, tube holders 12, which hold tubes 11, are shown suspended from a radially-extending rotor yoke 15. The tube holders 12 are spaced apart from and balanced about the central axis of yoke 15. Balancing of the tube holders is generally accomplished by positioning tube holders with contents of equal mass symmetrically about the central axis. A tube holder may be balanced with a weight, however. For clarity, FIG. 2 shows only two tube holders and associated supports. The tube holders 12 are connected to the yoke 15 by pivots 13 and bearings 63. Thus, tube holder 12 may move about pivot 13.

The rotor yoke 15 may be connected to the rotor 26 via rotor extensions 60. Rotor 26, according to the first embodiment, is a hollow cylinder with projecting extensions 60 for support of yoke 15. Rotor 26 is driven by rotation motor 23 which connects to pulley 25 via armature shaft 57. Belt 21 surrounds rotor 26 and connects pulley 25 to rotor 26. The rotation motor 23 therefore drives the pulley 25 and belt 21 assembly and thereby drives the rotor 26 to cause rotation about the rotation axis. The rotation motor 23 thus controls the first phase of centrifugation according to the present invention.

Figure 4:
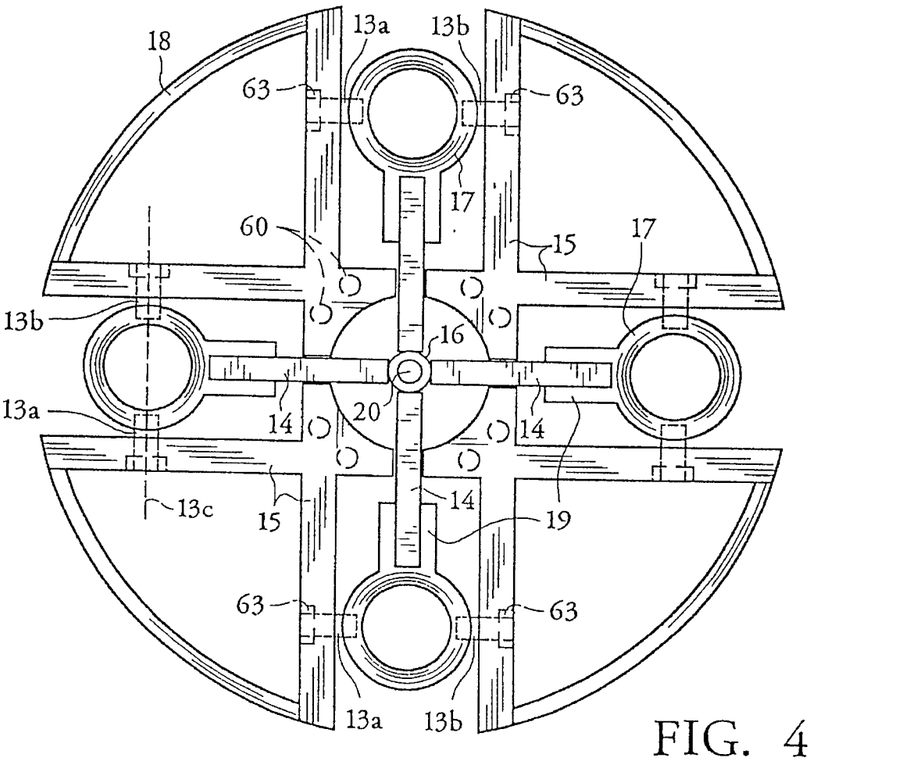
FIG. 4 is a top view of the centrifugation assembly of FIG. 2.

Also within the centrifugation assembly of the first embodiment is a shaft 20, which is driven to rotate about its central axis by inclination motor 24. About one end of the shaft 20 is a worm portion 16 of a worm gear. The worm 16 is in engagement with the teeth of various worm wheel segments 14. Each worm wheel segment 14 is operably connected to one of the tube holders 12, preferably through ring piece 17 and its extension 19, as seen in FIGS. 2 and 4. Rotation of shaft 20 by inclination motor 24 causes rotation of worm 16. In turn, rotation of worm 16 causes worm wheel segments 14 to travel relative to worm 16. Since the worm wheel segments 14 are fixedly attached to tube holders 12, movement of the worm wheel segments 14 causes movement of the tube holders 12 by pivoting of tube holders 12 about pivots 13. A cone drive gear may be an appropriate alternative to the worm gear.

Figure 3:
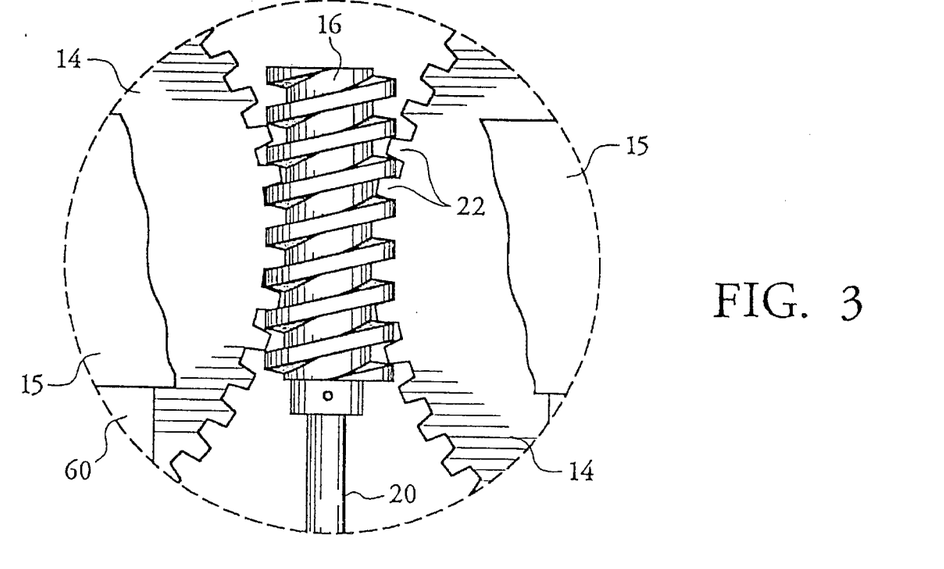
FIG. 3 is a detailed view of a section of FIG. 2, showing the worm gear of the first embodiment.

FIG. 3 presents an enlarged view of the worm gear operation, according to the first embodiment. In FIG. 3, teeth 22 of worm wheel segment 14 are clearly visible. By rotation of shaft 20 in a given direction and corresponding rotation of the worm in that direction, movement of the worm wheel segments 14 relative to the worm 16 occurs along the top halves of the worm wheel segments. Thus, tube holders 12 move about pivots 13, and are caused to incline with their top ends closer to the central or rotation axis of the centrifugation assembly than their bottom ends. Shaft 20 is physically located within rotor 26, as seen in FIG. 2, but the movement of shaft 20 is independent of the movement of rotor 26. Inclination motor 24 thus controls the second phase of centrifugation according to the present invention.

Rotor 26, shaft 20, and spindle 27 constitute the hub of the centrifugation assembly of the first embodiment, and may be supported on base 58 of FIG. 2. Spindle 27 is a fixed portion of the hub and serves to separate shaft 20 from rotor 26. Base 58 may serve to anchor spindle 27. Spindle 27 has an annular cross section, and in its simplest embodiment is a hollow cylinder. Shaft 20 is housed within spindle 27. Shaft 20 and spindle 27 are separated by bearings 28, which are preferably ball bearings. These bearings 28 allow shaft 20 to rotate freely within fixed spindle 27. Spindle 27 is itself positioned within rotor 26. Shaft 20, spindle 27, and rotor 26 have a common longitudinal axis. This is also coaxial with the central axis of yoke 15. As shown in FIG. 2, bearings 29 are positioned between spindle 27 and rotor 26. As with the bearings 28 between spindle 27 and shaft 20, the bearings 29 between spindle 27 and rotor 26 are preferably ball bearings. Rotor 26 is thus permitted to rotate freely about spindle 27. Because spindle 27 is fixed and separates the motion of shaft 20 from the motion of rotor 26, and because shaft 20 and rotor 26 are driven by independent motors, the centrifugation assembly of the first embodiment allows for independent control of rotation and inclination.

In operation, shaft 20 and rotor 26 should rotate synchronously to maintain a fixed inclination. If shaft 20 turns faster than rotor 26, the angle of inclination increases. If shaft 20 turns slower than rotor 26, the angle of inclination decreases. The high gear ratio available from the worm gear permits the limited torque of the inclination motor to maintain a fixed inclination at the high loads produced by rapid rotor rotation.

Unlike centrifuges of the prior art, for example, see U.S. Pat. No. 4,221,324 to Frey, the centrifugation assembly of the present invention does not include freely-swinging tubes or tube holders. Instead, inclination may be carefully controlled, both during rotation and, in the first embodiment, independent of rotation. Because the worm 16 is engaged with worm wheel segment 14 in the first embodiment, tube holders 12 may not freely swing about pivot 13. In the second and third embodiments of the centrifugation assembly of the present invention, strong springs may be utilized to control the rate and degree of inclination of the samples and prevent the tube holders from swinging freely about their pivots.

With reference to FIG. 4, rotor yoke 15 is shown as being capable of supporting multiple tube holders 12. FIG. 4 shows a cross-shaped yoke 15 capable of supporting four samples. In FIG. 2, two tube holders were shown for the sake of clarity. It is understood that rotor yoke 15 may be adapted for supporting two, four, or any other convenient multiple of tube holders. Additionally, yoke 15 may be adapted for supporting easily replaceable tube holders of varying shapes and sizes, including bucket-type holders for large sample containers. The tube holders may each hold more than one tube or sample.

FIG. 4 shows the top of shaft 20 having worm 16, and engagement of worm 16 with the worm wheel segments 14, one worm wheel segment 14 for each of the sample positions of the assembly. Worm wheel segments 14 are preferably semicircular plates having teeth along the outer periphery of the arced portion. The straight, non-toothed, portions of the worm wheel segments 14 are fixedly attached to tube holders 12. In FIG. 4, it is shown that this is advantageously accomplished through the use of ring pieces 17, wherein each ring piece 17 has an extension 19 for fixed attachment of a worm wheel segment 14. Each ring piece 17 may also serve as the support point for a pivot 13. For example, in FIG. 4, each pivot 13 is shown as two pieces 13a and 13b connecting ring piece 17 to yoke 15, comprising respective end pieces of a pivot shaft, and allowing movement of tube holder 12 about pivot axis 13c. Bearings 63, preferably ball bearings, may be used to support pivot 13 within yoke 15. Ring piece 17 may have tube holder 12 placed or attached within it. Alternatively, ring piece 17 may be an integral part of tube holder 12. A rim 18 is shown in the embodiment of FIG. 4 as connecting the various extensions of rotor yoke 15. This rim is not necessary, but may be desired for increased stability.

Figure 5:
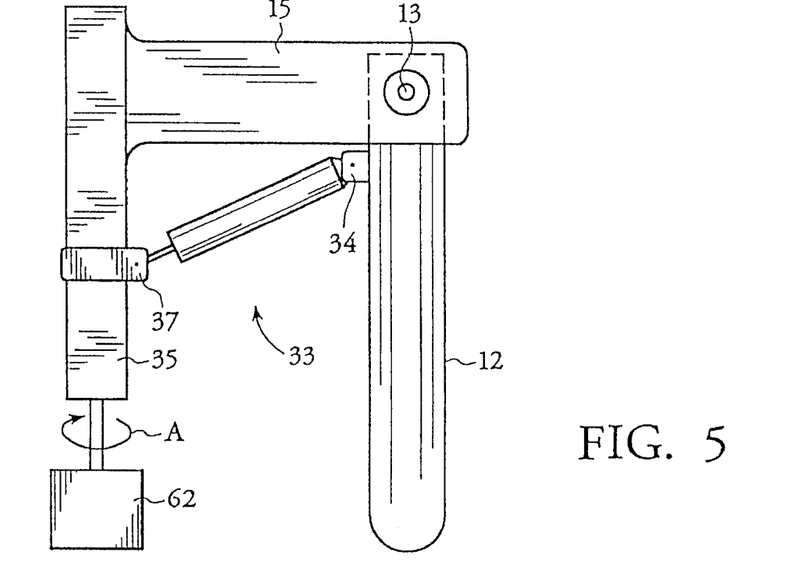
FIG. 5 is a side view of a portion of the centrifugation assembly according to the second embodiment of the present invention, showing a spring-loaded linkage and a tube holder in a first position.
Figure 6:
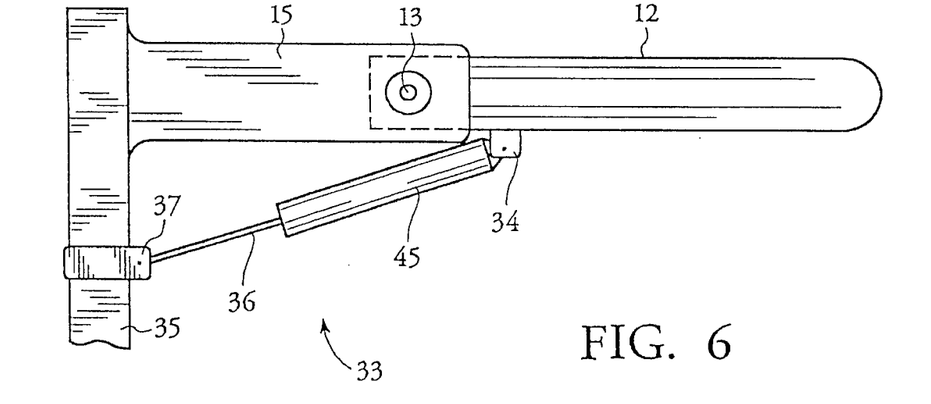
FIG. 6 shows a second position of the tube holder of FIG. 5 and the spring-loaded linkage in an extended position.
Figure 7:
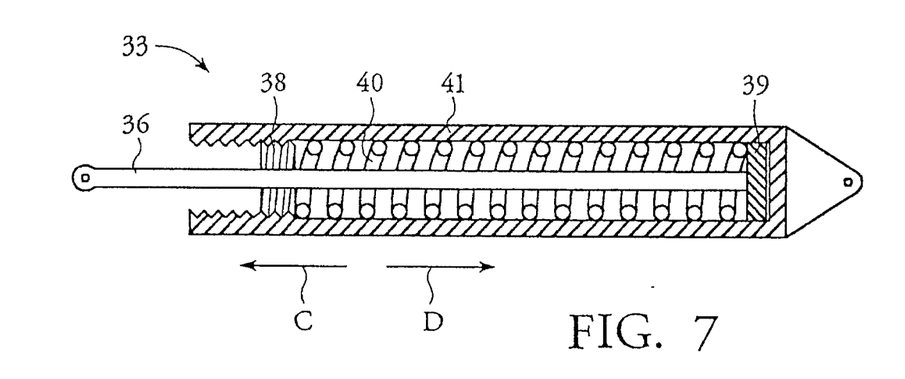
FIG. 7 is a sectional view of the spring-loaded linkage of FIGS. 5 and 6.

Referring to FIGS. 5 and 6, the centrifugation assembly according to the second embodiment of the present invention is shown. This second embodiment utilizes a spring-loaded linkage 33 to effect inclination, instead of a worm gear. In FIG. 5, the hub 35 of the centrifugation assembly is attached to rotor yoke 15. Hub 35 and yoke 15 may be of simpler construction in the second and third embodiments than in the first embodiment. For example, the hub of FIG. 5 may be a solid piece. As in the first embodiment, hub 35 is coaxial with the central axis of yoke 15. Tube holder 12 is shown supported from yoke 15 at pivot 13, as before. In the spring-loaded linkage system, an anchor ring 37 is shown disposed about hub 35. Spring-loaded linkage 33 is attached at one end to anchor ring 37 and an opposite end to tube holder 12, as by hinge piece 34 which is attached to tube holder 12. Alternatively, anchor ring 37 may be eliminated and the first end of each spring-loaded linkage 33 may be attached directly to hub 35. However, the anchor ring provides an advantage in that it may be fixed about hub 35 during processing of the samples, but may be moved and fixed at a higher or lower position along hub 35 for different sample runs, thereby affecting the inclination rate. Within a cylindrical housing 41 of spring-loaded linkage 33, as seen in FIG. 7, there are a compression spring 40 and an extension rod 36. The extension rod 36 is attached to a compression disk 39 within the housing 41 at one end. The other end of extension rod 36 extends from the housing 41 and is the point at which the spring-loaded linkage 33 is attached to anchor ring 37. Compression spring 40, compression disk 39, and a substantial portion of extension rod 36 are fitted within the cylindrical housing 41 of the spring-loaded linkage 33 by threaded adjustable bearing 38. Threaded adjustable bearing 38 centers extension rod 36 and adjusts the tension within housing 41 and thereby adjusts the rate of inclination of the tube holder 12.

At rest and during low speed rotation, as by rotation means 62, in the second embodiment of the centrifugation assembly, the tube holder 12 is held in the first position by the spring force of the spring-loaded linkage. The length of the spring-loaded linkage 33 is controlled by the force exerted by compression spring 40. As the speed of rotation of the samples increases, the forces arising from centrifugation overcome the spring force and allow extension rod 36 in combination with compression disk 39 to compress compression spring 40. This compression results in an extension of the length of spring-loaded linkage 33.

With reference to FIG. 7, compression of spring 40 and corresponding extension of extension rod 36 out of the housing 41 occurs in direction "C." Relative motion of the cylindrical housing 41 of spring-loaded linkage 33 occurs in direction "D."

FIG. 5 therefore represents centrifugation during the first phase of operation wherein the tube holders are held in the first position. FIG. 6 represents the second phase, wherein the tubes are inclined toward the second position, because centrifugal forces have overcome the spring force of compression spring 40 and allowed extension of spring-loaded linkage 33. Through the use of a spring having a high spring force, and through bearing 38, inclination can be controlled so that it occurs gradually. The length of the housing 41 and extension rod 36 should also be sized to allow smooth, kinematic movement of tube holder 12.

Figure 8:
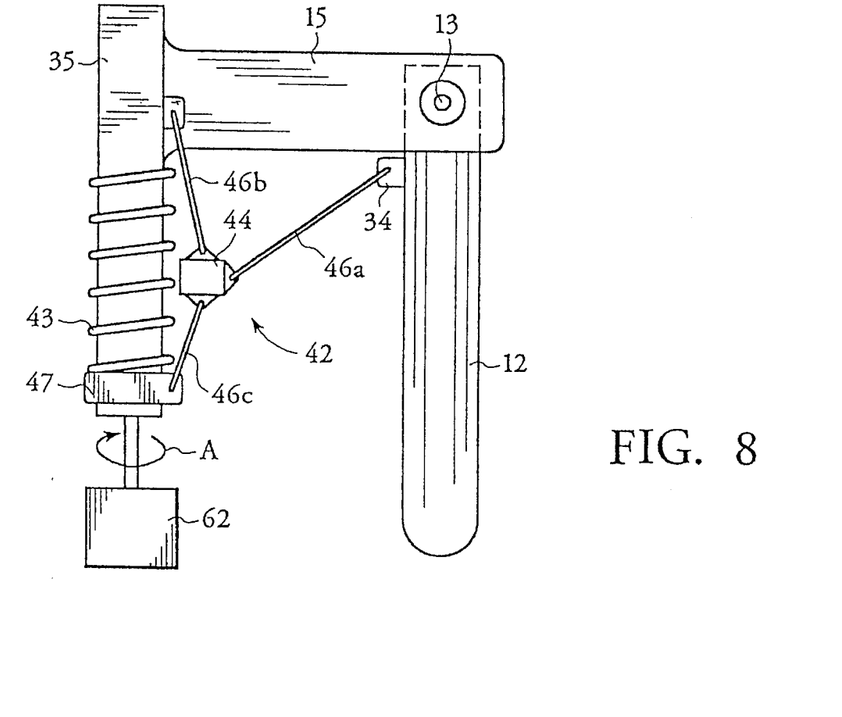
FIG. 8 is a side view of a portion of the centrifugation assembly according to the third embodiment of the present invention, showing a governor-based linkage and a tube holder in a first position.
Figure 9:
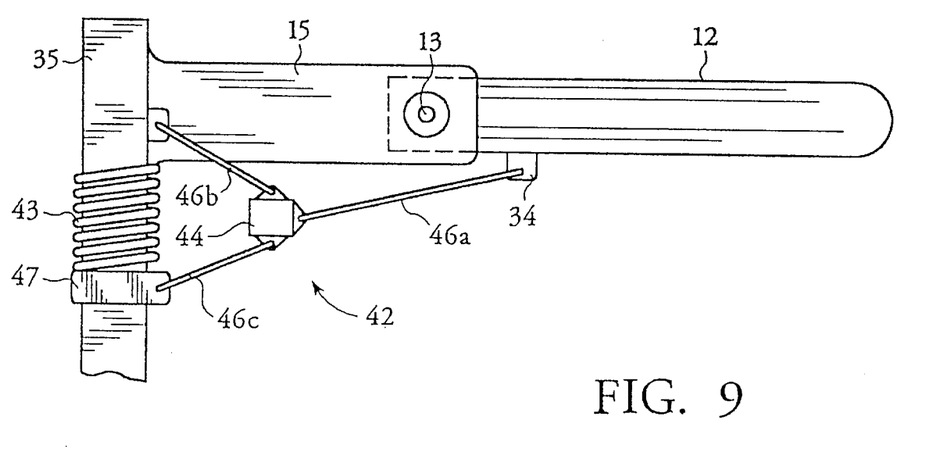
FIG. 9 shows a second position of the tube holder of FIG. 8 and the governor-based linkage in a radially extended position.

FIGS. 8 and 9, present a portion of the centrifugation assembly according to a third embodiment of the present invention. Other than the linkage system, the third embodiment is similar to the second embodiment. This third embodiment utilizes a governor-based linkage system to effect inclination. In particular, a governor-based linkage 42 includes a governor mass 44 and a set of three linking arms. The first arm 46a connects governor mass 44 to the tube holder 12, as by hinge piece 34. The second arm 46b is attached to the hub 35 or yoke 15 of the centrifugation assembly. The third arm 46c is attached to a sliding collar 47. Sliding collar 47 is disposed about hub 35. Also disposed about hub 35 is resistance spring 43.

In operation, resistance spring 43 pushes sliding collar 47 downward on hub 35 through its spring force, thereby retaining the tube holder 12 in the first position. As rotational velocity increases, however, the governor mass 44 is driven outward or radially from hub 35. This outward drive compresses resistance spring 43 in order to establish an equilibrium position for each speed. The force compressing the spring depends upon the mass and upon the radial position of the mass. The result is a first phase of centrifugation with tube holder 12 in the first position, as shown in FIG. 8. Tube holder 12 then moves toward the second position, as shown in FIG. 9, as the rotational velocity of the samples increases. Once again, through the use of a spring having a high spring force, inclination can be caused to occur gradually.

The sliding collar 47 also serves to synchronize the inclination rate of the various pivoting tube holders. This is important for dynamic balance of the assembly and smooth movement of the tube holders. Dynamic imbalance may result in ruined samples and a damaged assembly or centrifuge.

Figure 10:
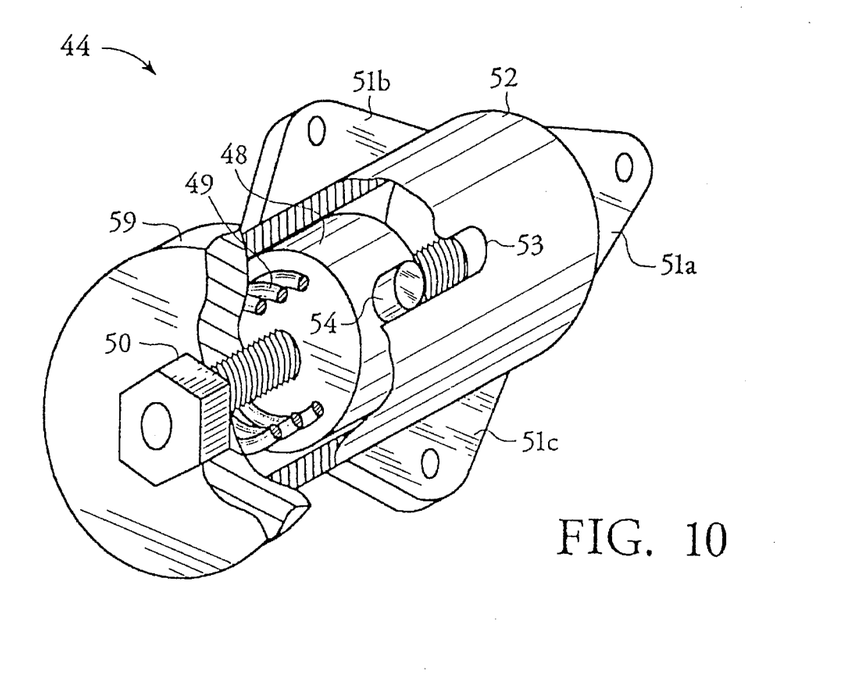
FIG. 10 is a perspective view with a partial cutaway of the governor mass of FIGS. 8 and 9.

FIG. 10 is a detailed partial cutaway view of the preferred governor mass 44 of the third embodiment of the present invention. Particularly, governor mass 44 includes a slotted cylindrical housing 52 which houses an adjustment mass 48 and a restoring spring 49. The radial position of the adjustment mass 48 is adjustable by turning adjusting screw 50 which moves adjustment mass 48 against restoring spring 49 and thereby adjusts the rate of inclination of the connected tube holder. At least one pin 54 mates adjustment mass 48 with a slot 53 in the cylindrical housing 52 to prevent rotation of adjustment mass 48 about the screw axis. The housing is closed by a threaded cap 59. The outside of cylindrical housing 52 is provided with arm link extensions 51a–c for connecting governor mass 44 with each of the three linking arms 46a–c.

Although only one tube holder 12 and one spring-loaded linkage 33 or one governor-based linkage 42 are depicted and described in the second and third embodiments respectively, each tube holder 12 supported on yoke 15 of the centrifugation assembly has an associated linkage. These linkages serve as the spring means for controlling the inclination of the samples during centrifugation. Rotation in these embodiments is via a simple rotation motor 62, shown in FIGS. 5 and 8, or by the rotation drive of the centrifuge into which the assemblies are installed.

Although an even number of tube holders positioned symmetrically about a yoke represents the preferred configuration for balance purposes in the three embodiments, a singular tube holder, or other odd number of tube holders, may be supported from the yoke of the centrifugation assembly. This odd-numbered configuration necessitates a properly-positioned counterbalance, however.

As stated above, the centrifugation assembly of the present invention need not be a fixed part of a centrifuge. This allows the assembly to be used in various standard centrifuges. Since standard blood draw tubes of glass or plastic may be utilized with the assembly, the result is a one-time cost of the assembly to laboratories and hospitals. The assembly may also be removed from the centrifuge for cleaning, sterilization, temperature control, or sample preparation in a protected environment.

Depending upon the details of the centrifuge that will incorporate the apparatus of the present invention, the three embodiments of the assembly may include a rotation motor or other means for rotating the samples about the central axis, as previously shown and described, or the assemblies may be rotor assemblies attachable to an existing rotation motor of the centrifuge. The unusual position of the rotation motor in the first embodiment, as compared to most standard centrifuges, generally indicates that an assembly with a rotation motor included and positioned as shown in FIG. 2 is likely to be the more useful variation of the first embodiment, however.

The three embodiments of the centrifugation or rotor assembly and the method for rapid separation of blood described herein represent a simple, yet significant, solution to the problems of high throughput blood processing.

We claim:
1. A method for rapid sample separation comprising:
providing at least one tube holder for holding the sample, each tube holder suspended from a yoke by a gradually adjustable pivot and balanced about the yoke,
initiating rotation of the samples about a central axis of the yoke while each tube holder is in a first position wherein the longitudinal axis of the tube holder is substantially parallel to the central axis of the yoke,
gradually and controllably adjusting the rate and amount of inclination of each tube holder toward a second position wherein the longitudinal axis of the tube holder is substantially perpendicular to the central axis of the yoke, while continuing rotation, and
maintaining a degree of inclination and a speed of rotation until separation of sample components is achieved.
2. The method of claim 1 further comprising:
gradually stopping rotation about the central axis of the yoke while returning the degree of inclination to the first position after separation of the sample components is achieved.
3. The method of claim 1 further comprising:
stopping rotation about the central axis of the yoke after separation of the sample components is achieved,
then returning the degree of inclination to the first position.
4. The method of claim 1 wherein the step of gradually and controllably adjusting the rate and amount of inclination further comprises:
providing a worm gear having a worm disposed about a shaft, the shaft being coaxial with the central axis of the yoke, and at least one worm wheel segment, each worm wheel segment being in engagement with the worm and being operably connected to one of the tube holders, and
rotating the shaft about the longitudinal axis of the shaft to operate the worm gear so as to cause each worm wheel segment to travel relative to the worm and thereby to cause inclination of each tube holder.

5. The method of claim 1 wherein the step of gradually and controllably adjusting the rate and amount of inclination further comprises:

providing at least one spring-loaded linkage, each spring-loaded linkage having a compression spring and an extension rod and being operably connected at a first end to one of the tube holders and at a second end to an anchor ring disposed about a hub, the hub being coaxial with the central axis of the yoke, each compression spring pushing against and limiting extension of one of the extension rods and retaining one of the tube holders in the first position until the rotational speed of the samples causes compression of each compression spring and corresponding extension of each extension rod and drives each tube holder outward from the central axis of the yoke.

6. The method of claim 1 wherein the step of gradually and controllably adjusting the rate and amount of inclination further comprises:

providing at least one governor-based linkage, each governor-based linkage having a governor mass and three arms extending outwardly from the governor mass, the governor mass being operably connected by the first arm of the linkage to one of the tube holders, by a second arm of the linkage to one of the group consisting of the yoke and a hub which is coaxial with the central axis of the yoke, and by a third arm of the linkage to a sliding collar disposed about the hub, providing a resistance spring disposed about the hub for pushing down on the sliding collar and retaining each tube holder in the first position until the rotational speed of the samples causes compression of the resistance spring and drives each governor mass and the connected tube holder outward from the central axis of the yoke.

7. A variable inclination centrifugation assembly for rapid sample separations comprising:

a yoke extending radially from a central hub, at least one pivoting tube holder supported by the yoke and balanced about the yoke, each pivoting tube holder being adapted for holding at least one sample, means for rotating each pivoting tube holder about the hub, and means for gradually adjusting the inclination of each pivoting tube holder from a first position wherein the longitudinal axis of each pivoting tube holder is substantially parallel to the longitudinal axis of the central hub toward a second position wherein the longitudinal axis of each pivoting tube holder is substantially perpendicular to the longitudinal axis of the hub.

8. The centrifugation assembly of claim 7 wherein the means for rotating each pivoting tube holder and the means for gradually adjusting the inclination of each pivoting tube holder are independently controlled.

9. The centrifugation assembly of claim 7 wherein the means for gradually adjusting the inclination of each pivoting tube holder is a worm gear having a worm disposed about a shaft, the shaft being coaxial with the hub, and at least one worm wheel segment, each worm wheel segment being in engagement with the worm and being operably connected to one of the pivoting tube holders, whereby operation of the worm gear by rotation of the shaft about the longitudinal axis of the shaft causes each worm wheel segment to travel relative to the worm and causes the connected pivoting tube holder to become inclined.

10. The centrifugation assembly of claim 7 wherein the means for gradually adjusting the inclination of each pivoting tube holder is a spring-loaded linkage system for retaining each pivoting tube holder in the first position at rest and for inclining each pivoting tube holder toward the second position when activated by the rotational speed of the samples, the spring-loaded linkage system having:

at least one spring-loaded linkage, each spring-loaded linkage having a compression spring and an extension rod and connected at a first end to one of the pivoting tube holders and at a second end to an anchor ring, the anchor ring disposed about the hub, each compression spring pushing against and limiting extension of one of the extension rods and retaining one of the pivoting tube holders in the first position until the rotational speed of the samples causes compression of each compression spring and corresponding extension of each extension rod and drives each pivoting tube holder outward from the hub.

11. The centrifugation assembly of claim 7 wherein the means for gradually adjusting the inclination of each pivoting tube holder is a governor-based linkage system for retaining each pivoting tube holder in the first position at rest and for inclining each pivoting tube holder toward the second position when activated by the rotational speed of the samples, the governor-based linkage system having:

at least one governor mass, each governor mass governing the position of one of the pivoting tube holders, at least one set of three arms, each set extending outwardly from one of the governor masses, the first arm connected to one of the pivoting tube holders, the second arm connected to one of the group consisting of the hub and the yoke, and the third arm connected to a sliding collar disposed about the hub, and a resistance spring disposed about the hub for pushing down on the sliding collar and retaining each pivoting tube holder in the first position until the rotational speed of the samples causes compression of the resistance spring and drives each governor mass and the connected pivoting tube holder outward from the hub.

12. A centrifugation assembly for rapid sample separations comprising:

a radially-extending yoke having a central axis, at least one pivoting tube holder, each pivoting tube holder spaced apart from the central axis, and supported by and balanced about the yoke, at least one worm wheel segment supported by the yoke, each worm wheel segment operably connected to one of the pivoting tube holders, a shaft disposed coaxially with the yoke and having a worm in engagement with each worm wheel segment for inclining each pivoting tube holder upon rotation of the shaft, means for rotating the shaft, and means for rotating the yoke about the central axis so as to cause centrifugation of contents of each pivoting tube holder.

13. The centrifugation assembly of claim 12 wherein the means for rotating the shaft and the means for rotating the yoke about the central axis are independently controlled.

14. A rotor assembly attachable to a rotation motor for rapid sample separations, the rotor assembly comprising:

a radially-extending yoke having a central axis, the yoke operably connectable to the rotation motor, at least one pivoting tube holder, each pivoting tube holder spaced apart from the central axis, and supported by and balanced about the yoke, at least one worm wheel segment supported by the yoke, each worm wheel segment operably connected to one of the pivoting tube holders, a shaft disposed coaxially with the yoke and having a worm in engagement with each worm wheel segment for inclining each pivoting tube holder upon rotation of the shaft, and an inclination motor for rotation of the shaft, whereby connection and operation of the rotation motor to the yoke causes rotation of the yoke about the central axis, and operation of the inclination motor causes inclination of each pivoting tube holder.

15. The rotor assembly of claim 14 wherein the inclination motor and the rotation motor are independently controlled.

16. A centrifugation assembly comprising:

a yoke extending radially from a central hub, at least one pivoting tube holder, each pivoting tube holder spaced apart from the hub, and supported by and balanced about the yoke, each pivoting tube holder being adapted for holding at least one sample, means for rotating each pivoting tube holder about the hub, and spring means for retaining each pivoting tube holder at rest in a first position wherein the longitudinal axis of the pivoting tube holder is substantially parallel to the longitudinal axis of the hub and for inclining each pivoting tube holder when activated by operation of the means for rotating and by the resulting rotational speed of the samples toward a second position wherein the longitudinal axis of the pivoting tube holder is substantially perpendicular to the longitudinal axis of the hub.

17. The centrifugation assembly of claim 16 wherein the spring means further comprises a spring-loaded linkage system having:

at least one spring-loaded linkage, each spring-loaded linkage having a compression spring and an extension rod and connected at a first end to one of the pivoting tube holders and at a second end to an anchor ring, the anchor ring disposed about the hub, each compression spring pushing against and limiting extension of one of the extension rods and retaining one of the pivoting tube holders in the first position until the rotational speed of the samples causes compression of each compression spring and corresponding extension of each extension rod and drives each pivoting tube holder outward from the hub.

18. The centrifugation assembly of claim 17 wherein each spring-loaded linkage further comprises a threaded adjustable bearing disposed against the compression spring and the extension rod, the threaded bearing for adjusting tension within the spring-loaded linkage and thereby adjusting the rate of inclination of the connected pivoting tube holder.

19. The centrifugation assembly of claim 17 wherein the anchor ring is fixed about the hub for operation of the assembly, but may be adjusted and fixed to any position along the hub for different operation runs.

20. The centrifugation assembly of claim 16 wherein the spring means further comprises a governor-based linkage system having:

at least one governor mass, each governor mass governing the position of one of the pivoting tube holders, at least one set of three arms, each set extending outwardly from one of the governor masses, the first arm connected to one of the pivoting tube holders, the second arm connected to one of the group consisting of the hub and the yoke, and the third arm connected to a sliding collar disposed about the hub, and a resistance spring disposed about the hub for pushing down on the sliding collar and retaining each pivoting tube holder in the first position until the rotational speed of the samples causes compression of the resistance spring and drives each governor mass and the connected pivoting tube holder outward from the hub.

21. The centrifugation assembly of claim 20 wherein each governor mass further comprises a slotted housing, an adjustment mass within the housing, a restoring spring within the housing, and a screw for moving the adjustment mass against the restoring spring for adjusting the position of the adjustment mass radially with respect to the hub, and thereby adjusting the rate of inclination of the connected pivoting tube holder.

22. The centrifugation assembly of claim 21 further comprising at least one pin coupled to each adjustment mass for mating the adjustment mass with the associated slotted housing to prevent rotation of the adjustment mass about the associated screw.

23. A rotor assembly attachable to a rotation motor, the rotor assembly comprising:

a yoke extending radially from a central hub, at least one pivoting tube holder, each pivoting tube holder spaced apart from the hub, and supported by and balanced about the yoke, each pivoting tube holder being adapted for holding at least one sample, and spring means for retaining each pivoting tube holder at rest in a first position wherein the longitudinal axis of the pivoting tube holder is substantially parallel to the longitudinal axis of the hub and for inclining each pivoting tube holder when activated by operation of the rotation motor and by the resulting rotational speed of the samples to a second position wherein the longitudinal axis of the pivoting tube holder is substantially perpendicular to the longitudinal axis of the hub.

24. The rotor assembly of claim 23 wherein the spring means further comprises a spring-loaded linkage system having:

at least one spring-loaded linkage, each spring-loaded linkage having a compression spring and an extension rod and connected at a first end to one of the pivoting tube holders and at a second end to an anchor ring, the anchor ring disposed about the hub, each compression spring pushing against and limiting extension of one of the extension rods and retaining one of the pivoting tube holders in the first position until the rotational speed of the samples causes compression of each compression spring and corresponding extension of each extension rod and drives each pivoting tube holder outward from the hub.

25. The rotor assembly of claim 23 wherein the spring means further comprises a governor-based linkage system having:

at least one governor mass, each governor mass governing the position of one of the pivoting tube holders, at least one set of three arms, each set extending outwardly from one of the governor masses, the first arm connected to one of the pivoting tube holders, the second arm connected to one of the group consisting of the hub and the yoke, and the third arm connected to a sliding collar disposed about the hub, and a resistance spring disposed about the hub for pushing down on the sliding collar and retaining each pivoting tube holder in the first position until the rotational speed of the samples causes compression of the resistance spring and drives each governor mass and the connected pivoting tube holder outward from the hub.

26. A variable inclination centrifugation assembly comprising:

(a) a fixed spindle having an annular cross-section and having a central axis, (b) a rotation subassembly including:
  (i) a rotor rotatably mounted about the spindle and having a central axis common to the spindle, and
  (ii) a rotation motor for driving the rotor about the spindle, (c) an inclination subassembly including:
  (i) a rotatable shaft mounted within the spindle and having a central axis common to the spindle,
  (ii) a worm disposed about a portion of the shaft,
  (iii) a plurality of worm wheel segments, each worm wheel segment having teeth for engaging the worm, and
  (iv) an inclination motor for rotating the shaft, (d) a plurality of pivoting tube holders, each pivoting tube holder operably connected to one of the worm wheel segments, (e) a yoke connected to the rotor and having a central axis common to the spindle, the yoke supporting the pivoting tube holders and the worm wheel segments,
  whereby operation of the rotation subassembly causes rotation of the pivoting tube holders about the central axis of the spindle and operation of the inclination subassembly causes the worm wheel segments to travel relative to the worm and to incline the pivoting tube holders.

27. The centrifugation assembly of claim 26 wherein operation of the rotation motor and of the inclination motor are independent.

* * * * *